Figure 1:
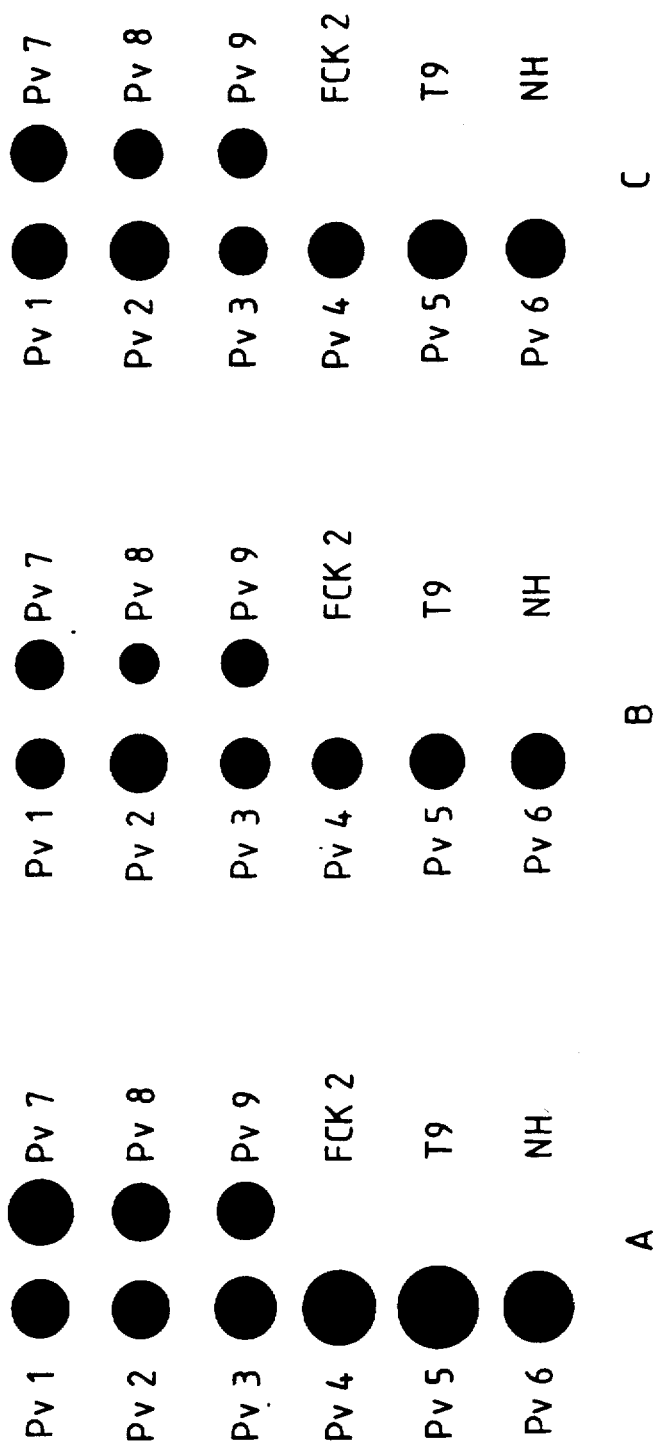

United States Patent [19]

Ayyanathan et al.

[11] Patent Number: 5,250,411
[45] Date of Patent: Oct. 5, 1993

[54] **NUCLEIC ACID PROBES SPECIFIC FOR *PLASMODIUM VIVAX* AND METHODS OF USING THE SAME**

[75] Inventors: K. Ayyanathan; P. Bhat; S. Datta; V. S. N. K. Francis; G. Padmanaban; H. Srinivasa, all of Bangalore, India

[73] Assignee: Aktiebolaget Astra, Sodertalje, Sweden

[21] Appl. No.: 624,313

[22] Filed: Dec. 4, 1990

[30] Foreign Application Priority Data

Dec. 5, 1989 [SE] Sweden ............... 8904100

[51] Int. Cl.⁵ ............ C12N 15/00; C12N 1/20; C12Q 1/68; C07H 15/12
[52] U.S. Cl. ............ 435/6; 435/172.3; 435/252.3; 435/320.1; 435/252.33; 536/74.32
[58] Field of Search ............ 435/6, 259, 172.3, 69.1, 435/252.3, 320.1, 349, 879, 911; 536/26, 27, 28; 935/77, 78

[56] References Cited

U.S. PATENT DOCUMENTS

| | | | |
|---|---|---|---|
| 4,358,535 | 11/1982 | Falkern et al. | 435/5 |
| 4,693,994 | 9/1987 | McCutchan et al. | 514/15 |
| 4,957,869 | 9/1990 | Arnot et al. | 435/320 |
| 5,061,788 | 5/1991 | Certa | 435/172.3 |
| 5,101,017 | 3/1992 | Rubinstein et al. | 530/388.22 |
| 5,112,749 | 5/1992 | Brey, III et al. | 435/172.3 |

FOREIGN PATENT DOCUMENTS

| | | |
|---|---|---|
| 0135108 | 3/1985 | European Pat. Off. |
| 0223711 | 5/1987 | European Pat. Off. |
| 8503725 | 8/1985 | PCT Int'l Appl. |
| 8700533 | 1/1987 | PCT Int'l Appl. |
| 8807546 | 10/1988 | PCT Int'l Appl. |

OTHER PUBLICATIONS

David et al. CA Abs. 109: 184635j vol. 109:182 (1988).
Gunderson et al. Science 238:933 (1987).
Arnot, et al., Science 230, pp. 815–817 (1985).
McCutchan, et al., Science 230, pp. 1381–1383 (1985).
Rosenberg, et al., Science 245, pp. 973–976 (1989).

*Primary Examiner*—Robert A. Wax
*Assistant Examiner*—Miguel Escallon
*Attorney, Agent, or Firm*—White & Case

[57] ABSTRACT

Disclosed are the DNA sequences of probes specific for *Plasmodium vivax* and the methods by which they were obtained. These nucleic acid sequences proved useful in detection of malaria in man caused by *P. vivax* by nucleic acid hybridization assays. The high sensitivity of these assays and the ease with which they can be performed enables them to be used for analyses of blood and other tissues of vertebrates and the invertebrates.

16 Claims, 1 Drawing Sheet

NUCLEIC ACID PROBES SPECIFIC FOR *PLASMODIUM VIVAX* AND METHODS OF USING THE SAME

BACKGROUND OF THE INVENTION AND PRIOR ACT

Malaria is caused by protozoan parasites belonging to the genus Plasmodium. The life cycle of the parasite occurs in two phases—the asexual phase in vertebrates and the sexual phase in the mosquito (usually of the genus Anopheles). The four species of Plasmodium responsible for human malaria are *P. falciparum, P. vivax, P. malariae* and *P. ovale.*

Among these, the first two are the most common. *P. falciparum* causes the most severe form of malaria which in some instances is fatal. Further, this parasite also develops resistance to commonly used antimalarial drugs. The frequency of the cases caused by *P. vivax* varies between different countries but generally it is about 50–80%. The occurrence of *P. malariae* and *P. ovale* is rare.

The current method of diagnosis of malaria is by blood smear examination. This method is laborious and also requires expertise. Further, a skilled microscopist is allowed to examine a maximum of sixty slides a day. Diagnosis by serology may also be done but because of the persistence of antibodies current infections cannot be distinguished from past infections. The search for a new generation of diagnostic tests includes the possibility of detecting parasite nucleic acids as indicative of the presence of the parasite. Such a test requires very little blood (5–50 ul) that can be obtained from a finger prick, is sensitive and rapid. As few as 50 parasites in 10 ul of blood can be detected by nucleic acid hybridization (1). Hundreds of samples can be analyzed in a day with some initial training. The sensitivity of the assay enables the test to be used in blood banks for the screening of blood to be used for transfusion.

Nucleic acid hybridization could also be performed on insect tissue samples in order to identify the vector species as a carrier. Such information would help to intensify vector control measures in order to limit the geographic spread of malaria. Alternatively, chemoprophylaxis may be adopted in such areas and evaluation of this strategy may be accomplished using nucleic acid hybridization.

Double stranded DNA is of complementary nature. Under certain conditions of temperature and salt concentration, the complementary strands of DNA may be denatured or dissociated and reproducibly reassociated. The reassociation, may also occur between DNA and complementary RNA. The reassociating DNA and RNA may be tagged with detection devices (isotopic or non-isotopic) and appropriate detection methods may be employed. In the case of *P. vivax*, there is no report of any potential DNA probe sequences. The development of specific nucleic acid sequences to detect *P. vivax* would be important in order to determine the incidence of *P. vivax* in a geographically defined area. The term 'probe' is used to denote a set of DNA sequences obtained biologically or synthetically.

Nucleic acid hybridization may be performed on any biological sample suspected of harbouring the parasite. Blood, for example, may be taken directly, solubilized in alkali and spotted on nitrocellulose or similar solid supports by standard methods (2). The DNA is immobilized on the supports and is brought in contact with the specific probe under appropriate conditions of temperature, ionic strength etc (3) which would favour specific reannealing of the probe and target nucleic acids. If the probe carries an isotopic tag (usually $^{32}P$), radioautography is performed to detect positive samples from negative ones. If the probe carries a non-isotopic tag e.g. biotin (4), an enzyme system e.g. avidin-alkaline phosphatase is employed and after a cascade of events colour develops in samples that are positive for the test.

In yet another technique (5), blood or the tissue sample to be analyzed may be collected directly in a chaotropic agent such as 4M guanidine thiocyanate. The hybridization process is performed in solution and the mixture is then filtered through a solid support under conditions which facilitate the binding of target-probe hybrids only while excess of probe does not bind to the matrix. Radioautography or colorimetric detection may be performed on this matrix. This hybridization format is especially useful when single stranded RNA probes are used.

DETAILS OF THE INVENTION

The present invention describes the identification of specific DNA sequences for *P. vivax* and the nucleotide sequences of these probes for *P. vivax*. Based on these characterizations, a diagnostic procedure for the specific detection of *P. vivax* has been developed employing nucleic acid hybridization. The test is rapid, sensitive and can be used on a large scale for purposes of epidemiological surveys.

The present invention relates to:

1. The new constructs or plasmids, pARC 117, pARC 145 and pARC 1153, deposited in the form of transformed *E. coli* at The National Collection of Industrial Bacteria Ltd., Torry Research Station, P.O. Box 31, 135 Abbey Road, Aberdeen, AB9 8DG, Scotland on dates and under deposition numbers as given below:

pARC 117: NCIB 40114, *E. coli* RR1 M15 pARC 117, Feb. 15, 1989 pARC 145: NCIB 40110, *E. coli* RR1 M15 pARC 145, Feb. 7, 1989 pARC 1153: NCIB 40108, *E. coli* RR1 M15 pARC 1153, Feb. 7, 1989.

2. The DNA sequences of pARC 117, pARC 145 and pARC 1153 and substructures thereof comprising at least 20 consequtive nucleotides.

3. A DNA probe for detection of *P. vivax*, consisting of the nucleotide sequence identified below for pARC 117.

4. A DNA probe for detection of *P. vivax*, consisting of the nucleotide sequence identified as SEQ ID NO: 1 in the Sequence Listing and identified below for pARC 145.

5. A DNA probe for detection of *P. vivax*, consisting of the nucleotide sequence identified as SEQ ID NO: 2 in the Sequence Listing and identified below for pARC 1153.

6. A method for the detection of *P. vivax* in a biological sample of vertebrates or invertebrates by hybridization of a probe comprising a nucleotide sequence identified as SEQ ID NO: 3 in the Sequence Listing and as identified for either of pARC 117, pARC 145 and pARC1153, in radioactive or non-radioactive labelled form with their respective homologous sequences in the *P. vivax* genome, and detecting the labelled probe which is bound to the *P. vivax* genome.

The present invention is exemplified by but not limited to the diagnosis of diseases. Epidemiological screening, forensic investigations, determination of food contamination, public health surveys, preventive medicine, veterinary and agricultural applications with regard to diagnosis of infectious agents may be covered by this disclosure.

Identification of DNA sequences specific for *P. vivax*

Since *P. vivax* has not yet been cultured in vitro, genomic DNA from this parasite was obtained from the blood of an infected patient. After removing as much of the buffy coat as possible, the genomic DNA was prepared by standard methods (6), digested with the enzyme Sau 3A cloned into the Bam H1 site of the known plasmid vector, pUC 18. Species specific DNA sequences were identified by screening duplicate filters with nick-translated *P. vivax* DNA and nick-translated normal human DNA in a differential screening format. Three specific probes of *P. vivax* designated pARC 117, pARC 145 and pARC 1153 were obtained and they were subcloned into the M13 vectors and their DNA sequence determined by di-deoxy chain termination method (7). None of them had any characteristic repetitive elements within the region sequenced. A computer based homology search utilising updated databanks such as Genbank and EMBL revealed no significant homology with any published nucleotide sequences. The highest homology was obtained with pARC 117 and rat parvalbumin (about 41%). This figure is insignificant for all practical purposes.

The said probes for *P. vivax*, were specific and did not cross react with isolates of *P. falciparum* (FIG. 1).

Description of the detection procedure using the specific *P. vivax* probes

There are two main procedures for nucleic acid hydridization. In one method, the sample nucleic acid is immobilized on a solid support while the probe sequence is in solution (2). In the other method, both the sample nucleic acid and the probe sequence and are in solution (5).

Thus, one nucleic acid hybridization assay involves spotting of the blood or tissue sample on a solid support e.g. nitrocellulose which is then hydridized with the probe (isotopically/non-isotopically tagged) under appropriate conditions of temperature etc (3). This method is well documented and in the context of malaria diagnosis has been used by many investigators (8). However, the tissue sample has to be processed for parasite DNA extraction and then used in the dot blot assay. This is not desirable in the design of a diagnostic assay that is to be used for mass screening. In the experience of the inventors, direct spotting of infected blood on the matrix was not satisfactory. Erythrocyte membrane proteins and other plasma components in the blood, presumably proteins, and other tissues when used sterically hinder the binding of parasite DNA to the matrix. Consequently, during the hybridization process the spotted sample detaches from the matrix leading to a loss of specific signal. The problem may be overcome by prior washing of the samples to remove the interfering plasma constituents which will make the test laborious or by spotting very small amounts of the blood which would contribute to loss of sensitivity of detection.

The inventors have therefore, resorted to a solution hybridization format which requires no sample processing and is more rapid to perform than the filter hybridization format. The test utilises the following steps:

a) Tissue sample is collected directly in a solution of a chaotropic salt or a denaturing agent e.g. 25 ul of blood in 50 ul of 6M guanidine thiocyanate. If the probe has an isotopic tag, guanidine thiocyanate at a concentration of 4M can be used as the chaotropic salt. If the probe is non-isotopic (e.g. biotin) and has to be detected by an enzyme reaction, guanidine thiocyanate cannot be used since it binds to nitrocellulose, polyvinylidene difluoride (PVDF) filters and other similar matrices and denatures the enzyme conjugate subsequently used in the reaction. Guanidine thiocyanate can however, be used with non-isotopic probes provided the matrices are pretreated.

In the present invention, when guanidine hydrochloride is used as a solubilizing agent, it is found to be as effective as guanidine thiocyanate. It has the added advantage that it does not bind to the solid matrix and can therefore be used for non-isotopic probes.

b) The probe (1 ng) is added. The probe added is preferably a single stranded nucleic acid, DNA or RNA which may be obtained biologically or synthetically by methods well documented in the art. RNA is the preferred probe.

c) The sample is heated at 85° C. for five minutes and allowed to cool at room temperature (about 28°-35° C.) for two hours.

d) The sample is then diluted at least ten fold with a salt solution containing RNAseA and incubated for a further fifteen minutes. When single stranded DNA is used as the probe, unhybridized probe may be removed by hydroxylapatite chromatography.

e) The sample is then filtered through the matrix e.g. nitrocellulose or polyvinylidene fluoride filters and the filters are rinsed twice in salt solution containing RNAse A for fifteen minutes each time.

f) The appropriate detection method is then carried out.

Preparation of hybridization probes

The hybridization probes may be prepared by cloning the genomic elements in suitable vectors. These vectors may be plasmids (*E. coli* plasmids), filamentous phages (M13), lamboid bacteriophage, cosmids, salmonella phages and yeast. Any vectors documented in the art may be employed.

Hybridization probes may be labelled radioactively by nick-translation with $^{32}P$ using DNA Polymerase and [α-$^{32}P$] dNTP. For non radioactive labelling Bio-dUTP can be used in nick-translation reaction. Short oligonucleotide probes can be end-labelled with [α-$^{32}P$] or [α-$^{32}P$] dNTP at their 5' or 3' termini respectively.

Single stranded DNA probes labelled with $^{32}P$ can be obtained using the M 13 vector system (9). Single stranded DNA probes can be labelled with biotin by the polymerase chain reaction in presence of Bio-dUTP, other deoxyribonucleotides and Taq DNA polymerase (10).

In hybridization assays utilising RNA hybridization labelled RNA, complementary to DNA is prepared. Methods for the construction of such systems are well documented in the art (11). The present invention includes also such assays. The present invention thus includes the use of double-stranded DNA, single-stranded DNA, and RNA as probes for detecting the *P. vivax* genome.

EXAMPLE 1

This example illustrates the method by which species specific probes for *P. vivax* were obtained.

1. Total DNA from *P. vivax* infected blood was isolated, digested with the enzyme Sau 3A and cloned in the Bam H1 site of plasmid vector, pUC 18.
2. Clones were replica spotted on two filters of nitrocellulose. One filter was screened with nick-translated radioactive human DNA and the other filter was screened with nick-translated radioactive *P. vivax* DNA.
3. The hybridized replicas were autoradiographed to produce hybridization signals.
4. Clones that reacted with *P. vivax* DNA and not with human DNA were considered as species specific and were selected for use as hybridization probes for *P. vivax*.

5. In this way, three clones were identified. These clones are denoted pARC 117, pARC 145, and pARC 1153 respectively. The nucleotide sequences of the three clones are given and identified as SEQ ID NO: 1, SEQ ID NO: 2 and SEQ ID NO: 3, respectively, in the Sequence Listing. The nucleotide sequence of each clone was determined by standard methods with the following result.

```
5'·········AT GTA AGA GCA CAT
GAG ATT TTA TAA GGA TTT CAT TTT
ACT CAG GGT GAA ATG AAG AAG CAC
TAA AAG ATT TTG AGT AGA GTT TCA
T·······3'
```

```
5'·········CC AAG TGA AGA AAG
GTG GAA GGG CCA GCA GGA GAG CTG
GTC ACT GCA TTG TCT CTC TGA GGT
CTG TAG GCC AGA AGC TCC CCA GGA
CTT AGA CCC TAC TAA ATG GGG TAG
AGA GTA AGG GGC AGC CAT CAC TTA
TCA CTG GCT GTC CTG AGG GTT TGG
TGT ACA GCA TGG CTT GTG GTC AGA
GGC CTG TCA GCT GGG CTC CAA GAG
TCC TAG TGA ATG TAA ACA GTG CAG
ACC TTT TCT GGG GGG AAG G······3'
```

```
5'········TTT GTG TGA TTT TTG TGA TTT TTG ATG
GAA ACC TGA ATA TTT GGG GTA ATT ATG TGA TTA GAC
TCA GGA TTT TAT TTA AAT CTT CTG TTT TAG CTA GCC
TCC TCT GAC ACT AGC TTG GCA GGA ACG AGG GCA GGA
GAG CAT TGC TGA TGC ATT CCT GCC TCT TTT CTT CCT
TGT TAC TCC CAA GTG GGT GTA AAA ATC CAG GTT TCC
CAC TGT TTC CTC CTT TAA ATT AAT TAA TTA ATT TTT
AAT GTT GGC AAA TAA AAA TTA TAT ATT GTG TAT ATT
TAT GGG GTA CAA CAT GAT ATT TTG ATA TAT GTA TAC
ATT GCA GAA TGG CTA AAT TAA GCT AAT TAA CAT ACA
TAT TAC CTC ACA TAA TCA ATT TTT TTG TGG TGA GAG
CAC CTG CAA TCT ACT CTT TTA GCA ATT TTC AAG TAT
ATA AAA CAT TGT TAT TAA CTA TGG TCA CCT CAT TGT
ACA ATA TGT TTT TTG AAC TTA TTC CTC CTA AGT ATA
ATT TTG TAC TCT TTG ACC AAC ATC TCC CCA GAC CCC
TCA ATG CCC ACC CTC TGG TAA CCA ACA TTC TAC TCT
TTG CTT TTC AAC TTT TAT AGA TTC CAT ATG AAG TAG
GAT CAT GCT GTA TTT GTC TTT GTG CCT GGC TTA TTT
CCT TTA CAT ACT GTT CTC TAG GTG·········3'
```

EXAMPLE 2

This example illustrates the preparation of specific hybridization probes.

Hybridization probes were made by labelling the insert DNA in pARC 117, pARC 145 and pARC 1153 by nick translation in the presence of *E. coli* DNA polymerase or T4 DNA polymerase and [α−$^{32}$P] dNTPs yielding a specific activity of $10^7$ cpm to $5 \times 10^7$ cpm ug DNA. Single stranded or synthetically derived DNA may be end labelled at the 5' ends using polynucleotide kinase and [α−$^{32}$P] ATP. They may also be labelled at the 3' ends using terminal transferase and [α−$^{32}$P] dNTPs. Biotinylated single stranded DNA may be synthesised by the polymerase chain reaction employing Taq DNA polymerase and Bio-dUTP.

Single or double stranded nucleic acids may be biotinylated by photoactivatable biotin. Chemical biotinylation of nucleic acid may also be done.

Single stranded RNA may be generated by fusing the DNA of interest to a fragment of the Salmonella phage SP6 promoter in a suitable vector. The vector may be propagated in *E. coli*. DNA of this vector can be transcribed in vitro using the SP6 RNA polymerase. During this process radioactive RNA of high specific activity may be obtained using [$\alpha-^{32}P$] UTP. Biotinylation of this RNA is also possible.

EXAMPLE 3

This example illustrates the species specificity of the three *P. vivax* clones described in example 1, viz., pARC 117, pARC 145 and pARC 1153.

Genomic DNAs of nine different isolates of *P. vivax* were prepared and spotted on nitrocellulose filter. The filter was probed with the respective *P. vivax* specific probes which were radioactive. The probes reacted only with *P. vivax* samples and not with *P. falciparum* nor human DNA (FIG. 1).

EXAMPLE 4

This example illustrates the assay for *Plasmodium vivax* using a solution hybridization format.

Infected blood (20 ul) or tissue is taken directly into 50 ul of guanidine thiocyanate containing 1 ng of pARC 117 RNA probe radiolabelled as described in Example 2.

The sample is heated at 85° C. for five minutes and left at room temperature for two hours.

The sample is then diluted ten fold in 2×SSC containing 10 ng RNAse A and incubated at room temperature for a further 15 minutes.

The sample is then filtered through a nitrocellulose or polyvinylidene difluoride filter matrix and the filter rinsed in 2×SSC containing RNAse A buffer twice for 15 minutes each.

The filter is dried and autoradiographed to film for hybridization signals to develop.

The assay described is easy to perform and requires very little laboratory equipment such as is likely to be present in peripheral field conditions during mass surveys.

EXAMPLE 5

This example illustrates the solution hybridization procedure employing guanidine hydrochloride instead of guanidine thiocyanate as described in Example 4.

4M guanidine thiocyanate as the chaotrope and non-radioactive probes that are detected by protein conjugates are incompatible. The chaotropic salt binds to nitrocellulose and PVDF filters and denatures the protein conjugates that are used for colour development.

Guanidine hydrochloride when used as a solubilising agent is as effective as guanidine thiocyanate. Since it does not bind to the matrix (nitrocellulose or polyvinylidene difluoride filters), it enables the use of non-radioactive probes that are detected by protein conjugates.

Guanidine thiocyanate may be used in conjunction with non radioactive probes as described earlier only if the filter is pretreated, e.g. with 3% BSA before the guanidine thiocyanate solution is filtered through it.

REFERENCES

1. Pollack, Y., Metzger, S., Shemer, R., Landau, D., Spira, D. T. and Golenser, J. (1985). *Am. J. Trop. Med. Hyg.* 34, 663.
2. Kafatos, F. C., Jones, C. W. and Efstratiadis, A. (1979) *Nucl. Acids. Res* 7, 1541.
3. Maniatis, T., Fritsch, E. F. and Sambrook, J., *Molecular Cloning, A Laboratory Manual*, Cold Spring Harbour, N.Y. 1982.
4. Langer, P. R., Waldorp, A. A. and Ward, D. C. (1981) *Proc. Natl. Acad Sci.* U.S.A. 78, 6633.
5. Thompson, J. and Gillespie, D. (1987) *Anal. Biochem.* 163, 281.
6. Panyim, S., Wilairat, P. and Yuthavong, Y. *Application of Genetic Engineering to Research on Tropical Disease Pathogens with special reference to Plasmodia*-WHO publication.
7. Sanger, F., Coulson, A. R., Barrell, B. G., Smith, A. G. H. and Roe, B. A. (1980). *J. Mol. Biol.* 143, 161.
8. Holmberg, M., Bjorkmann, A., Franzen. L., Aslund, L., Lebbad, M., Pettersson U. and Wigzell, H. (1980), *Bull.* W.H.O. 64, 579.
9. Burke, J. F., (1984) *Gene* 30, 63.
10. Saiki, R. K., et al (1988) *Science* 239, 487.
11. Green, M. R., Maniatis, T. and Melton, D. A. (1983), *Cell* 32, 681.

FIGURE LEGEND

FIG. 1: Specificity of the *P. vivax* probes pARC 117 (A), pARC 145 (B) and pARC 1153 (C). Double stranded inserts isolated from the three clones were tested as probes. Pv1 to Pv9 represent DNA preparations from nine *P. vivax* infected blood samples. FCK 2 and T 9 represent *P. falciparum* DNA preparations. NH represent Normal human DNA.

---

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 87 base pairs
        ( B ) TYPE: nucleic acid
        ( C ) STRANDEDNESS: both
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:

(A) ORGANISM: Plasmodium vivax (vii) IMMEDIATE SOURCE:
    (B) CLONE: pARC 117

(xi) SEQUENCE DESCRIPTION: SEQ ID NO:1:

```
ATGTAAGAGC ACATGAGATT TTATAAGGAT TTCATTTTAC TCAGGGTGAA ATGAAGAAGC      60
ACTAAAAGAT TTTGAGTAGA GTTTCAT                                         87
```

(2) INFORMATION FOR SEQ ID NO:2:

(i) SEQUENCE CHARACTERISTICS:
        (A) LENGTH: 249 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Plasmodium vivax (vii) IMMEDIATE SOURCE:
        (B) CLONE: pARC 145

(xi) SEQUENCE DESCRIPTION: SEQ ID NO:2:

```
CCAAGTGAAG AAAGGTGGAA GGGCCAGCAG GAGAGCTGGT CACTGCATTG TCTCTCTGAG      60
GTCTGTAGGC CAGAAGCTCC CCAGGACTTA GACCCTACTA AATGGGGTAG AGAGTAAGGG     120
GCAGCCATCA CTTATCACTG GCTGTCCTGA GGGTTGGTG TACAGCATGG CTTGTGGTCA     180
GAGGCCTGTC AGCTGGGCTC CAAGAGTCCT AGTGAATGTA AACAGTGCAG ACCTTTCTG     240
GGGGGAAGG                                                             249
```

(2) INFORMATION FOR SEQ ID NO:3:

(i) SEQUENCE CHARACTERISTICS:
        (A) LENGTH: 663 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Plasmodium vivax (vii) IMMEDIATE SOURCE:
        (B) CLONE: pARC 1153

(xi) SEQUENCE DESCRIPTION: SEQ ID NO:3:

```
TTTGTGTGAT TTTTGTGATT TTTGATGGAA ACCTGAATAT TGGGGTAAT TATGTGATTA       60
GACTCAGGAT TTTATTTAAA TCTTCTGTTT TAGCTAGCCT CCTCTGACAC TAGCTTGGCA     120
GGAACGAGGG CAGGAGAGCA TTGCTGATGC ATTCCTGCCT CTTTTCTTCC TTGTTACTCC     180
CAAGTGGGTG TAAAAATCCA GGTTTCCCAC TGTTTCCTCC TTTAAATTAA TTAATTAATT     240
TTTAATGTTG GCAAATAAAA ATTATATATT GTGTATATTT ATGGGTACA ACATGATATT     300
TTGATATATG TATACATTGC AGAATGGCTA AATTAAGCTA ATTAACATAC ATATTACCTC     360
ACATAATCAA TTTTTTTGTG GTGAGAGCAC CTGCAATCTA CTCTTTTAGC AATTTTCAAG     420
TATATAAAAC ATTGTTATTA ACTATGGTCA CCTCATTGTA CAATATGTTT TTTGAACTTA     480
```

| TTCCTCCTAA | GTATAATTTT | GTACTCTTTG | ACCAACATCT | CCCCAGACCC | CTCAATGCCC | 540 |
| ACCCTCTGGT | AACCAACATT | CTACTCTTTG | CTTTCAACT | TTTATAGATT | CCATATGAAG | 600 |
| TAGGATCATG | CTGTATTTGT | CTTTGTGCCT | GGCTTATTTC | CTTTACATAC | TGTTCTCTAG | 660 |
| GTG | | | | | | 663 |

We claim:

1. The construct pARC 117, deposit no. NCIB 40114.
2. The construct pARC 145, deposit no. NCIB 40110.
3. The construct pARC 1153, deposit no. NCIB 40108.
4. An isolated and purified DNA fragment having the sequence identified as SEQ ID NO: 1 in the Sequence Listing and given below:

```
5'---------AT GTA AGA GCA CAT
GAG ATT TTA TAA GGA TTT CAT TTT
ACT CAG GGT GAA ATG AAG AAG CAC
TAA AAG ATT TTG AGT AGA GTT TCA
T-------3'
```

5. An isolated and purified DNA fragment having the sequence identified as SEQ ID NO: 2 in the Sequence Listing and given below:

```
5'---------CC AAG TGA AGA AAG
GTG GAA GGG CCA GCA GGA GAG CTG
GTC ACT GCA TTG TCT CTC TGA GGT
CTG TAG GCC AGA AGC TCC CCA GGA
CTT AGA CCC TAC TAA ATG GGG TAG
AGA GTA AGG GGC AGC CAT CAC TTA
TCA CTG GCT GTC CTG AGG GTT TGG
TGT ACA GCA TGG CTT GTG GTC AGA
GGC CTG TCA GCT GGG CTC CAA GAG
TCC TAG TGA ATG TAA ACA GTG CAG
ACC TTT TCT GGG GGG AAG G------3'
```

6. An isolated and purified DNA fragment having the sequence identified as SEQ ID NO: 3 in the Sequence Listing and given below:

```
5'---------TTT GTG TGA TTT TTG TGA TTT TTG ATG
GAA ACC TGA ATA TTT GGG GTA ATT ATG TGA TTA GAC
TCA GGA TTT TAT TTA AAT CTT CTG TTT TAG CTA GCC
TCC TCT GAC ACT AGC TTG GCA GGA ACG AGG GCA GGA
GAG CAT TGC TGA TGC ATT CCT GCC TCT TTT CTT CCT
TGT TAC TCC CAA GTG GGT GTA AAA ATC CAG GTT TCC
CAC TGT TTC CTC CTT TAA ATT AAT TAA TTA ATT TTT
AAT GTT GGC AAA TAA AAA TTA TAT ATT GTG TAT ATT
TAT GGG GTA CAA CAT GAT ATT TTG ATA TAT GTA TAC
ATT GCA GAA TGG CTA AAT TAA GCT AAT TAA CAT ACA
TAT TAC CTC ACA TAA TCA ATT TTT TTG TGG TGA GAG
CAC CTG CAA TCT ACT CTT TTA GCA ATT TTC AAG TAT
ATA AAA CAT TGT TAT TAA CTA TGG TCA CCT CAT TGT
ACA ATA TGT TTT TTG AAC TTA TTC CTC CTA AGT ATA
ATT TTG TAC TCT TTG ACC AAC ATC TCC CCA GAC CCC
TCA ATG CCC ACC CTC TGG TAA CCA ACA TTC TAC TCT
TTG CTT TTC AAC TTT TAT AGA TTC CAT ATG AAG TAG
GAT CAT GCT GTA TTT GTC TTT GTG CCT GGC TTA TTT
CCT TTA CAT ACT GTT CTC TAG GTG---------3'
```

7. A hybridization probe comprising a nucleotide sequence as defined in claims 4, 5 or 6 or a contiguous segment thereof which will specifically hybridize to *P. vivax* genome.

8. A hybridization probe according to claim 7 in an appropriate vector.

9. A hybridization probe according to claim 8, wherein the said vector is selected from *E. coli* plasmids, filamentous phages (M13), lamboid bacteriophages, cosmids, Salmonella phages and yeast.

10. A hybridization probe according to claim 9 wherein the said vector is an *E. coli* plasmid.

11. A hybridization probe according to claim 10 wherein the said *E. coli* plasmid is pUC 18 or pUC 19.

12. A hybridization probe according to claim 9 wherein the said vector contains a salmonella SP 6 phage promoter or a T7 phage promoter.

13. A hybridization probe according to claim 7, which probe is labelled with $^{32}P$, $^{125}I$, a chromophoric group or a reporter group.

14. A hybridization probe according to claim 13 wherein the said reporter group is biotin.

15. A method for detecting *P. vivax* in a biological sample of vertebrates or invertebrates, by hybridization of a probe according to claim 7 with the respective homologous sequences in the *P. vivax* genome, and detecting the probe which is bound to the *P. vivax* genome.

16. A method according to claim 15 wherein the said hybridization probe comprises a vector containing the said sequence of DNA, complementary DNA (single stranded) or RNA.

* * * * *

UNITED STATES PATENT AND TRADEMARK OFFICE
CERTIFICATE OF CORRECTION

PATENT NO. : 5,250,411
DATED : October 5, 1993
INVENTOR(S) : Ayyanathan et al.

It is certified that error appears in the above-indentified patent and that said Letters Patent is hereby corrected as shown below:

col. 2, line 49, after "sequence" insert --identified as SEQ ID NO: 1 in the Sequence Listing, and--;

col. 2, line 52, change "1" to --2--;

col. 2, line 56, change "2" to --3--;

col. 3, line 41, after "sequence", delete "and".

Signed and Sealed this

First Day of September, 1998

*Attest:*

BRUCE LEHMAN

*Attesting Officer*    Commissioner of Patents and Trademarks